United States Patent

Morris

(10) Patent No.: US 8,835,518 B2
(45) Date of Patent: Sep. 16, 2014

(54) PROCESS FOR THE TREATMENT OF AN ION EXCHANGE RESIN

(75) Inventor: Trevor Huw Morris, Durham (GB)

(73) Assignee: Lucite International UK Limited, Southampton (GB)

(*) Notice: Subject to any disclaimer, the term of this patent is extended or adjusted under 35 U.S.C. 154(b) by 0 days.

(21) Appl. No.: 13/259,951

(22) PCT Filed: Mar. 25, 2010

(86) PCT No.: PCT/GB2010/050510
§ 371 (c)(1),
(2), (4) Date: Nov. 18, 2011

(87) PCT Pub. No.: WO2010/109244
PCT Pub. Date: Sep. 30, 2010

(65) Prior Publication Data
US 2012/0059073 A1    Mar. 8, 2012

(30) Foreign Application Priority Data
Mar. 27, 2009    (GB) .................................. 0905257.2

(51) Int. Cl.
B01J 49/00    (2006.01)

(52) U.S. Cl.
USPC .............. 521/26; 560/211; 562/599; 210/677

(58) Field of Classification Search
USPC .............. 521/26; 560/211; 562/599; 210/677
See application file for complete search history.

(56) References Cited

U.S. PATENT DOCUMENTS

| 3,037,052 A | 5/1962 | Bortnick |
| 3,146,258 A | 8/1964 | Leach |
| 4,237,303 A | 12/1980 | Gatling |
| 4,447,641 A * | 5/1984 | Hagen ........................... 560/211 |

(Continued)

FOREIGN PATENT DOCUMENTS

| CN | 101311158 A | 11/2008 |
| EP | 0 343 583 A2 | 11/1989 |

(Continued)

OTHER PUBLICATIONS

Examination Report issued by the Intellectual Property Office of New Zealand issued in Application No. NZ 594983 dated Aug. 10, 2012.

(Continued)

*Primary Examiner* — Peter D. Mulcahy
*Assistant Examiner* — Henry Hu
(74) *Attorney, Agent, or Firm* — Venable LLP; Keith G. Haddaway; Annette K. Kwok

(57) ABSTRACT

A process for the reactivation of an acidic ion exchange resin is described. The invention relates to the treatment of an at least partially deactivated resin which has been deactivated by contact with an impure ethylenically unsaturated acid or ester containing target impurities. The reactivation includes the step of contacting the at least partially deactivated resin with an alcohol to thereby increase the activity thereof. The invention extends to reactivating a resin deactivated by contact with an impure ethylenically unsaturated acid, ester or nitrile containing target impurities by contacting the at least partially deactivated resin with an alcohol and a carboxylic acid to thereby increase the activity thereof. A reactivated resin and a process for preparing and purifying an ethylenically unsaturated acid or ester of the following formula: $-R^1-C(=(CH_2)_m)-COOR^2$ are also described.

15 Claims, 1 Drawing Sheet

(56) References Cited

U.S. PATENT DOCUMENTS

| | | | |
|---|---|---|---|
| 4,581,471 A * | 4/1986 | Barlow et al. | 560/210 |
| 4,625,059 A | 11/1986 | Shibano et al. | |
| 4,733,004 A | 3/1988 | Pascoe | |
| 4,970,344 A * | 11/1990 | Keller | 564/497 |
| 5,006,258 A * | 4/1991 | Veatch et al. | 210/677 |
| 5,034,558 A | 7/1991 | Yoshioka et al. | |
| 5,043,518 A | 8/1991 | Michaelson et al. | |
| 7,812,187 B2 | 10/2010 | Kawashima et al. | |
| 8,350,081 B2 | 1/2013 | Balduf | |

FOREIGN PATENT DOCUMENTS

| | | | |
|---|---|---|---|
| EP | 343583 A2 * | 11/1989 | |
| JP | 57-187042 A | 11/1982 | |
| JP | 58-183641 | * 10/1983 | |
| JP | 58-183641 A | 10/1983 | |
| JP | 60-006635 A | 1/1985 | |
| JP | 62-42748 A | 2/1987 | |
| JP | 63-107755 A | 5/1988 | |
| JP | 01-139547 A | 6/1989 | |
| JP | 01-299254 A | 12/1989 | |
| JP | 04-507368 A | 12/1992 | |
| JP | 10-072379 A | 3/1998 | |
| JP | 2003-261504 A | 9/2003 | |
| JP | 2003-277317 A | 10/2003 | |
| JP | 2005-179483 A | 7/2005 | |
| JP | 2007-014871 | * 1/2007 | |
| JP | 2007-014871 A | 1/2007 | |
| WO | WO-03/099756 A1 * | 12/2003 | |
| WO | WO-03/099756 A1 | 12/2003 | |
| WO | WO-2007/088702 A1 | 8/2007 | |
| WO | WO-2008/078769 A1 * | 7/2008 | |
| WO | WO-2008/078769 A1 | 7/2008 | |
| WO | WO-2008/145418 A1 | 12/2008 | |
| WO | WO-2010/070325 A1 | 6/2010 | |
| WO | WO-2010/109244 A2 * | 9/2010 | |

OTHER PUBLICATIONS

International Preliminary Report on Patentability issued in International Application No. PCT/GB2010/050510 dated Sep. 27, 2011.
International Search Report issued in International Application No. PCT/GB2010/050510 dated Nov. 18, 2010.
Office Action issued in Chinese Application No. 201080013154.4 dated Feb. 20, 2013.
Office Action issued in Chinese Application No. 201080013154.4 dated Aug. 9, 2013.
Office Action issued in Australian Application No. 2010227277 dated Aug. 30, 2013.
Further Examination Report issued by the Intellectual Property Office of New Zealand issued in Application No. NZ 594983 dated Nov. 22, 2013.
Letter dated Nov. 15, 2013 reporting Office Action issued in Mexican Application No. MX/a/2011/009543.
Office Action issued in Russian Patent Application No. 2011143366/05 dated Mar. 4, 2014.
Office Action issued in Japanese Patent Application No. 2012-501388 dated Apr. 1, 2014.
Office Action issued in Chinese Patent Application No. 201080013154.4 dated Feb. 13, 2014.
Office Action issued in Chinese Patent Application No. 201080013154.4 dated Jun. 6, 2014.
Office Action and Search Report issued in Taiwanese Patent Application No. 099109235 dated Jul. 4, 2014.

* cited by examiner

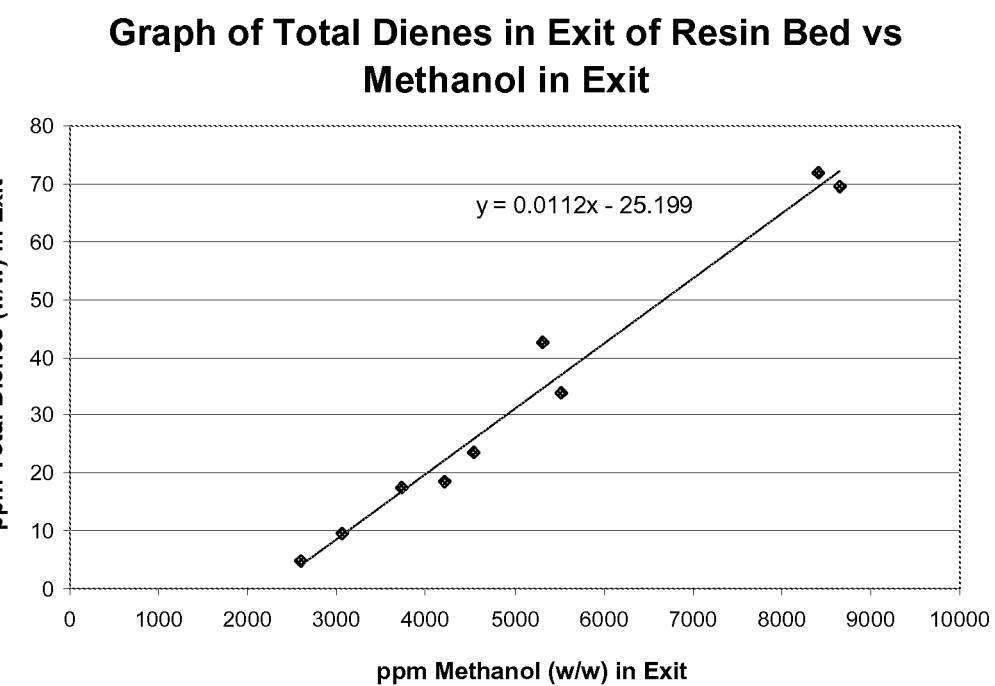

PROCESS FOR THE TREATMENT OF AN ION EXCHANGE RESIN

This application is a U.S. National Stage of International Application number PCT/GB2010/050510, filed Mar. 25, 2010, which claims the benefit of British Application number 0905257.2, filed Mar. 27, 2009.

The present invention relates to a process for the treatment of an ion exchange resin, in particular, the reactivation of a deactivated acidic ion exchange resin.

BRIEF DESCRIPTION OF THE DRAWINGS

FIG. 1. A plot of total diene output versus methanol output on a resin bed treated according to an embodiment of the invention.

Co-pending unpublished patent application GB0823075.7 demonstrates that an acidic ion exchange resin may be used for removing impurities from an impure MMA stream, and that the activity of the resin bed declines after a few days, but may be maintained for prolonged periods by inclusion of formaldehyde in the feed stream either as free formaldehyde or in a form which liberates formaldehyde in the presence of the acidic ion exchange resin.

Japanese Laid Open patent 58-183641, Japanese patent application 63-127952 and U.S. Pat. No. 4,625,059 relate to purification of MMA using ion exchange resins. None of these publications give any teaching on the degradation of the activity of the resin or how to reactivate a deactivated resin.

The use of acidic ion exchange resins for the esterification of acrylic and methacrylic acid to form esters is known in the art. An example is U.S. Pat. No. 3,037,052 which describes the general methodology for use of acidic ion exchange resins for esterification of unsaturated acids with olefins.

U.S. Pat. No. 4,733,004 teaches that esterification using methanol as a solvent in excess over stoichiometric ratio to acid assists in the prevention of polymer formation in a fluidised bed of ion exchange resin.

However the prior art does not provide any teaching on the reactivation of resins which have lost activity during esterification of unsaturated acids or during purification of unsaturated acids or esters.

U.S. Pat. No. 4,237,303 relates to the removal of oxazole from acrylonitrile using an acidic ion exchange column. The document teaches that the resin can be regenerated using 1N $H_2SO_4$, deionised water and steam. Although regeneration with methanol is also shown, the efficacy shown for regeneration with methanol is significantly inferior to that for water or $H_2SO_4$ and is more than 30 times poorer to that of steam under the same conditions.

Surprisingly, we have now found that an ion exchange resin may be reactivated to close to its initial activity by treating a deactivated resin with an alkanol or with a mixture of an alkanol and a carboxylic acid and that this reactivation process may be undertaken many times with little or no loss in activity to the resin bed. In this way the useful life of the resin bed may be extended from a period of a few days to many months. This extension in the life of the resin bed is particularly advantageous in continuous or semi-continuous processes.

According to a first aspect of the present invention there is provided a process for the reactivation of an acidic ion exchange resin that has been at least partially deactivated by contact with an impure ethylenically unsaturated acid or ester containing target impurities comprising the steps of:— contacting the at least partially deactivated resin with at least one $C_1$-$C_{12}$ aliphatic alkanol to thereby increase the activity thereof.

According to a further aspect of the present invention there is provided a process for the reactivation of an acidic ion exchange resin that has been at least partially deactivated by contact with an impure ethylenically unsaturated acid, ester or nitrile containing target impurities comprising the steps of:— contacting the at least partially deactivated resin with at least one $C_1$-$C_{12}$ aliphatic alkanol and at least one carboxylic acid to thereby increase the activity thereof.

Preferably, the contact of the alkanol and acid with the deactivated resin also results in the production of the corresponding ester of the alkanol and acid. It is thus advantageous to use the said ester in the production of the impure ethylenically unsaturated acid or ester prior to the purification of the latter to thereby allow the use of the reactivation step ester in a continuous process. Accordingly, the alkanol and ester are preferably selected so that they react to form an ester in the presence of the said resin which ester will react with a source of formaldehyde to form the said impure ethylenically unsaturated acid or ester.

Accordingly, the invention relates to a two step resin treatment process wherein the resin is used to remove impurities from a first feed stream in a first purification step until it is deactivated and then the resin is reactivated by a second feed stream in a separate reactivation step. Thus necessarily, the compositions of the first and second feed streams are distinct and different. Advantageously, the product of the reactivation step using the second feed stream may be recycled as an ester reactant in the production of the first feed stream where the first feed stream is produced from such an ester and other reactants.

Resin

The acidic ion exchange resin may be strong or weakly acidic but is preferably, strongly acidic. Preferably, the acidic ion exchange resin is a sulphonic acid ion exchange resin.

The acidic ion exchange resin may be a gel or macroreticular resin. Preferably, the sulphonic acid resin comprises a strongly acidic, macroporous, polymer based resin. Most preferably, the sulphonic acid resin comprises a crosslinked polystyrene resin in spherical bead form with bead size 0.4 to 1.64 mm, with between 0.5 and 3.0 equivalents per liter of sulphonic acid groups (preferably between 0.7 and 2.5) with a large pore structure with mean pore diameter between 15 nm and 90 nm (preferably between 20 nm and 70 nm), surface area between $15\,m^2g^{-1}$ and $100\,m^2g^{-1}$ (preferably between 20 $m^2g^{-1}$ and 80 $m^2g^{-1}$) and a pore volume measured by the extent of water retention per unit of wet resin of between 30 and 80% (preferably 40-70%). Preferably, the acidic ion exchange resin is macroreticular resin.

Reactivation

Preferably, the acidic ion exchange resin is in the form of a packed resin bed. Therefore, the alkanol or alkanol and carboxylic acid is typically, contacted with the deactivated resin by passing a volume of alkanol or alkanol and carboxylic acid, sufficient to at least partially reactivate the resin bed, through the bed.

Typically, the resin bed is at least 10% reactivated by the process of the invention, more typically, at least, 40% reactivated, most typically, at least, 70% reactivated. It is especially typical to find that the contact with the alkanol or more especially, alkanol and carboxylic acid causes the resin to be over 90% reactivated and even over 95% reactivation is not unusual. Accordingly, the invention extends to substantially full reactivation of the deactivated resin.

It will be understood that the volume of alkanol or alkanol and carboxylic acid is such as will cause the deactivated bed to be sufficiently reactivated and to sufficiently remove the accumulated impurities. Typically, at least 1 bed volume of alkanol or alkanol and carboxylic acid is passed through the resin bed, more typically, at least 2 bed volumes, most typically, at least 3 bed volumes.

Preferably, at least one carboxylic acid is also present in the reactivation process. The carboxylic acid may be added together with the alkanol or may be added separately. Preferably, it is pre-mixed with the alkanol prior to contact with the deactivated resin. Typically, the carboxylic acid and the alkanol are fully miscible and intimately mixed prior to contact with the deactivated resin. Generally, it may be advantageous if the acid and alkanol react on the surface of the resin to produce the corresponding ester and water. Typically, in a continuous or semi-continuous process the at least one carboxylic acid is already available as a by-product of the ethylenically unsaturated acid, ester or nitrile production. Typically, the at least one carboxylic acid is added to the reactivation stream in a continuous or semi-continuous process to form part of a combined liquid reactivation stream. It should be understood that the carboxylic acid whether produced as a by-product in the production of the impure ethylenically unsaturated acid, ester or nitrile or not, will generally not be present in the impure ethylenically unsaturated product which deactivates the resin.

Typically, in the case of an impure ethylenically unsaturated ester, there is no carboxylic acid present in the deactivating product. This is undesirable because of a possible competing transesterification reaction between the carboxylic acid and the impure ester product. Accordingly, any carboxylic acid produced as a by-product in the production of an ethylenically unsaturated ester will be preferably removed from the impure product prior to its contact with the resin. Thereafter, carboxylic acid may be introduced to the resin for reactivation purposes. For the purposes of precise definition, in the above case, there is less than 1% w/w carboxylic acid in the impure ethylenically unsaturated ester prior to resin contact, more preferably, less than 0.5% w/w, most preferably, less than 0.1% w/w.

Deactivation

In a continuous process, after a suitable period which could, for example be a 1 or 2 weeks or 1 or 2 months the efficacy of an acid resin may have reduced to less than 20% of its efficacy when fresh. This is often referred to as a "deactivated" resin. Preferably, by an at least partially deactivated resin is meant a resin which has had its ability to react, with one or more target impurities in an impure product which is contacted with the resin, reduced by prolonged exposure to resin contaminants and/or the target impurities. If the resin is in the form of a resin bed, the impure product and the reactivation treatment will be in the form of feed streams which are passed through the bed.

Preferably, an at least partially deactivated resin has less than 99.9% efficacy (target impurity conversion yield) as compared to its efficacy when fully activated. Preferably, an at least partially deactivated resin has less than 99% efficacy as compared to its efficacy when fully activated, more typically, less than 95% efficacy, most typically, less than 90% efficacy, especially, less than 85% efficacy. For example, typically, the at least partially deactivated resin has less than 80% efficacy, for example, 70%, 60% or 50% efficacy in reacting with at least one target compound as compared to its efficacy when fully activated and ready for use.

By fully activated is meant fresh resin that has been activated according to the manufacturer's recommended procedure, for instance, a resin that has been washed with 1-5, preferably, 3 bed volumes of alcohol, for example, methanol followed by 1-3, preferably, 2 bed volumes of a stream of pure ethylenically unsaturated ester, acid or nitrile, for example, MMA.

Target Impurities

The invention has been found to be particularly useful in the reactivation of resins which have been used to treat one or more organic target impurities in the impure ethylenically unsaturated liquid which treatment has led to deactivation of the resin. It has been found that suitable organic target impurities include unsaturated organic compounds, for example, $C_1$ to $C_{20}$ hydrocarbons optionally containing one or more heteroatoms (nitrogen, oxygen, sulphur). A preferred family of target impurities are the optionally substituted $C_4$-$C_{20}$ dienes. The invention has been found to be particularly useful for resins which have been deactivated by such dienes. Useful substituted dienes that can be used as target impurities in the present invention are $C_{0-6}$ mono-tetra alkyl $C_4$-$C_{12}$ dienes, such as $C_4$-$C_8$ dienes, for example, mono or dialkyl hexadienes. Examples of such dienes have been found to include but are not restricted to any of the following: 2-methyl-1,5-hexadiene; trans 2-methyl-2,4-hexadiene; cis 2-methyl-2,4-hexadiene; 2-methyl-3,5-hexadiene; 2-methyl-1,3-hexadiene; 2,5-dimethyl-1,3-hexadiene and 1,6-heptadiene, especially, trans 2-methyl-2,4-hexadiene and cis 2-methyl-2,4-hexadiene.

In addition, the target impurities may also be selected from optionally substituted $C_6$-$C_{14}$ trienes. Examples of trienes include but are not restricted to any of the following: heptatriene, cycloheptatriene.

The invention has been found to be especially efficient for deactivated resins which have been deactivated after contact with $C_4$-$C_{20}$ dienes or $C_6$-$C_{20}$ trienes with one or more substituted, preferably, alkyl, more preferably, $C_{1-6}$ alkyl substituted, internal enyl carbons or di-substituted, preferably, alkyl, more preferably, $C_{1-6}$ alkyl substituted, terminal enyl carbons which enyl carbons are thereby capable of forming tertiary carbocations.

Other impurities that may be removed by the practice of the present invention also typically comprise optionally substituted unsaturated aldehydes and ketones. Examples of such aldehyde or ketone compounds include R'C=OR" wherein R' can be hydrogen, optionally substituted alkyl, alkenyl or aryl more preferably, $C_{1-6}$ alkyl, $C_{1-6}$ alkenyl or aryl and R" can be optionally substituted alkyl, alkenyl or aryl, more preferably, $C_{1-6}$ alkyl, $C_{1-6}$ alkenyl or phenyl.

Suitable further target impurities include: divinyl ketone, ethyl vinyl ketone, ethyl isopropenyl ketone, 3-methylene 1-hexen-4-one, methacrolein, isobutanol, and pentenals such as 3-pentenal.

A still further target impurity that may deactivate the resin is a source of isobutyraldehyde. The source of isobutyraldehyde may be isobutyraldehyde itself or a compound which generates isobutyraldehyde when exposed to the ion exchange resin. Examples of such compounds include the mono or di-acetals of isobutyraldehyde with a C1 to C6 branched or non-branched alcohol, in particular 1,1-dimethoxy-2-methyl propane, as well as 2-methylpropenol, which is an isomer of isobutyraldehyde.

The term "alkyl" when used herein, means unless otherwise indicated, $C_1$ to $C_{10}$, preferably, $C_1$ to $C_4$ alkyl and alkyl includes methyl, ethyl, propyl, butyl, pentyl, hexyl, and heptyl groups. Unless otherwise specified, alkyl groups may, when there is a sufficient number of carbon atoms, be linear or branched (particularly preferred branched groups include t-butyl and isopropyl), be saturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $SR^{29}$, $C(O)SR^{30}$, unsubstituted or substituted aryl, or unsubstituted or substituted Het, wherein $R^{19}$ to $R^{30}$ each independently represent hydrogen, halo, unsubstituted or substituted aryl or unsubstituted or substituted alkyl, or, in the case of $R^{21}$, halo, nitro and cyano and/or be interrupted by one or more (preferably less than 4) oxygen, sulphur, silicon atoms, or by silano or dialkylsilicon groups, or mixtures thereof.

The term "Ar" or "aryl" when used herein, includes five- to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $SR^{29}$ or $C(O)SR^{30}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro or cyano.

The term "alkenyl" when used herein, means $C_2$ to $C_{10}$ alkenyl and includes ethenyl, propenyl, butenyl, pentenyl, and hexenyl groups. Unless otherwise specified, alkenyl groups may, when there is a sufficient number of carbon atoms, be linear or branched, be cyclic, acyclic or part cyclic/ acyclic, be unsubstituted, substituted or terminated by one or more substituents selected from halo, cyano, nitro, $OR^{19}$, $OC(O)R^{20}$, $C(O)R^{21}$, $C(O)OR^{22}$, $SR^{29}$, $C(O)SR^{30}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilicon groups, or mixtures thereof.

Halo groups with which the above-mentioned groups may be substituted or terminated include fluoro, chloro, bromo and iodo.

The term "Het", when used herein, includes four- to twelve-membered, preferably four- to ten-membered ring systems, which rings contain one or more heteroatoms selected from oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, $C(O)OR^{22}$, —$SR^{29}$ or —$C(O)SR^{30}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro or cyano. The term "Het" thus includes groups such as optionally substituted lactonyl, furanyl and thiophenyl. Substitution at Het may be at a carbon atom of the Het ring or, where appropriate, at one or more of the heteroatoms.

The term "hetero" as mentioned herein means oxygen, sulphur or mixtures thereof.

It will be understood that the process of the present invention is not the same as washing an untreated resin. Washing an untreated resin with an alcohol is relatively commonplace. The advantage of the present invention arises from the surprising reactivation of a deactivated resin by treatment with alkanol or alkanol and carboxylic acid.

Preferably, the impure ethylenically unsaturated product of the present invention may be produced by any suitable process known to those skilled in the art. One particular process for which the present invention has been found to be particularly advantageous is the condensation of formaldehyde with methyl propionate to produce MMA. It has been found that the present invention is particularly advantageous in the removal of impurities from liquid MMA produced by such a process.

Preferably, the alkanol or alkanol and carboxylic acid is introduced to the resin in the form of a reactivation liquid. The molar concentration of the total alkanol in the reactivation liquid is at least 10 mol %, more typically, at least 30 mol %, most typically at least 40 mol % and, in any case, preferably, up to 100 mol %, more preferably, up to 75 mol %, most preferably, up to 50 mol %. For instance a suitable reactivation liquid may be, for example, 100 mol % alkanol or up to 50 mol % alkanol and up to 50 mol % carboxylic acid. The total carboxylic acid molar concentration in the reactivation liquid is preferably, up to 70 mol %, more preferably, up to 60 mol %, most typically, up to 40 mol % and, in any case, at least 2.5 mol %, more preferably, at least 5 mol %, and most preferably, at least 10 mol %, especially, at least 20 mol %. Other components are not necessary but may also be present as minor components. For instance, the ethylenically unsaturated product may be present as a minor component of the reactivation liquid. Typically, these other components in combination are present at up to 50 mol %, more typically up to 40 mol %, most typically, up to 30 mol %, for example 10-30 mol % of the reactivation liquid.

Preferably, the weight percentage of the particular alkanol(s) in the reactivation liquid is in accordance with that of the mole percents above and depends on the molecular weights of the various components in the reactivation liquid. In the most preferred process where MMA is the impure liquid and methanol and optionally propionic acid are the main components of the reactivation liquid, methanol is at least 5% w/w, more typically, at least 15% w/w, most typically, at least 20% w/w of the reactivation liquid and in any case, up to 100% w/w, more preferably, up to 40% w/w, most preferably, up to 30% w/w methanol in the reactivation liquid. For instance, a suitable reactivation liquid may be, for example, 100% alkanol(s) or 25% alkanol(s) and 50% carboxylic acid(s). The propionic acid concentration in the reactivation liquid is up to 95% w/w, more typically, up to 80% w/w, most typically, up to 60% w/w and, in any case, at least 5% w/w, when present, more preferably, at least 10% w/w and most preferably, at least 25% w/w, especially, at least 40% w/w when present.

Suitable alkanols for use generally in the present invention are $C_1$-$C_{12}$, preferably $C_1$-$C_{10}$ aliphatic alkanols. Unless otherwise specified, the aliphatic alkanols may, when there is a sufficient number of carbon atoms, be linear or branched, be saturated, unsaturated, be cyclic, acyclic or part cyclic/acyclic, be unsubstituted, substituted or terminated by one or more substituents selected from alkyl, aryl, Het, halo, cyano, nitro, $OR^{19}$, $OC(O)R^{20}$, $C(O)R^{21}$, $C(O)OR^{22}$, $SR^{29}$ or $C(O)SR^{30}$ as defined herein. Highly preferred alkanols are the relatively polar $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably selected from di-octa ols such as diols, triols and tetra-ols may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol and 1,1,1 tri(hydroxymethyl)ethane. Especially preferred alkanols are $C_1$ to $C_4$ alkyl alcohols such as methanol and ethanol. The most preferred alkanol is methanol. For the avoidance of doubt, the alkanols are non-aromatic.

Suitable carboxylic acids for use in the present invention are selected from any straight or branched $C_2$ to $C_{12}$, more preferably, $C_2$-$C_8$, most preferably, $C_2$-$C_6$ carboxylic acid. Unless otherwise specified, the acid may, when there is a sufficient number of carbon atoms, be aliphatic or aromatic, part aromatic/aliphatic, linear or branched, be saturated, unsaturated, be cyclic, acyclic or part cyclic/acyclic, be unsubstituted, substituted or terminated by one or more substituents independently selected from those defined for the alkanols above. The or each at least one carboxylic acid is most preferably selected from any branched or unbranched $C_2$ to $C_4$ carboxylic acid. Examples of suitable saturated carboxylic acids include but are not restricted to acetic acid, propionic acid, butanoic acid and isobutyric acid. In a preferred embodiment, propionic or isobutyric acid are also present in the reactivation process. Examples of suitable unsaturated carboxylic acids include methacrylic acid and acrylic acid. In some embodiments, it may be advantageous to use a mixture of carboxylic acids chosen from those above. A particularly preferred combination of carboxylic acids is an unsaturated carboxylic acid and a saturated carboxylic acid. A suitable mole ratio of unsaturated to saturated carboxylic acid is between 1:4 and 4:1. An especially advantageous mixture is propionic acid and methacrylic acid. Preferably, the alkanol, in conjunction with a carboxylic acid may conveniently react to form the ester of the acid. For instance, a mixture of methanol and propionic acid would react to form methyl propionate. Thus, in addition to reactivating the acidic ion exchange resin bed the alkanol and the carboxylic acid react to form a useful by-product such as methyl propionate in the case of methanol and propionic acid.

Advantageously, in the purification of an ethylenically unsaturated acid or ester produced via the reaction of a suitable methylene source, for example, formaldehyde or a suitable source thereof in the presence of a catalyst with a carboxylic ester, the resin reactivating alkanol and carboxylic acid may be selected so that they form the said carboxylic ester and can thus be recycled as a reactant in the production process.

The ethylenically unsaturated acid or ester is preferably represented by the following formula:—

wherein $R^1$ and $R^2$ are each, independently, hydrogen or an alkyl group with 1 to 12, more preferably, 1 to 8, most preferably, 1 to 4 carbon atoms.

The ethylenically unsaturated nitrile is preferably represented by the following formula:—

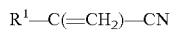

wherein $R^1$ is defined in the same way as for the ethylenically unsaturated acid or ester above.

A suitable process for preparing the ethylenically unsaturated acids or ester comprises contacting an alkanoic acid or ester of the formula $R^1$—$CH_2$—$COOR^3$, with a suitable source of methylene or ethylene of formula as defined below:

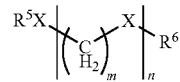

where $R^5$ and $R^6$ are independently selected from $C_1$-$C_{12}$ hydrocarbons, preferably, $C_1$-$C_{12}$ alkyl, alkenyl or aryl as defined herein, or H, more preferably, $C_1$-$C_{10}$ alkyl, or H, most preferably, $C_1$-$C_6$ alkyl of H, especially, methyl or H; X is either O or S, preferably, O;
n is an integer from 1 to 100, preferably, 1 to 10, more preferably 1 to 5, especially, 1-3;
and m is 1 or 2, preferably 1;
in the presence of a suitable catalyst, and optionally in the presence of an alkanol; wherein $R^1$ is as defined for the ethylenically unsaturated acid or ester above and $R^3$ may also be independently, hydrogen or an alkyl croup with 1 to 12, more preferably, 1 to 8, most preferably, 1 to 4 carbon atoms.

In a particularly preferred embodiment the compound of formula I is derived from formaldehyde in the presence of methanol and/or water. In such a case, the compound of formula I may be defined as a suitable source of formaldehyde.

For the avoidance of doubt, a suitable source of formaldehyde includes any equilibrium composition which may provide a source of formaldehyde. Examples of such include but are not restricted to methylal (1,1 dimethoxymethane), polyoxymethylenes —$(CH_2$—$O)_i$— wherein i=1 to 100 formalin (formaldehyde, methanol, water) and other equilibrium compositions such as a mixture of formaldehyde, methanol and methyl propionate.

Typically, the polyoxymethylenes are higher formals of formaldehyde and methanol $CH_3$—O—$(CH_2$—$O)_i$—$CH_3$ ("formal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—$(CH2$-O—$)_iR^{32}$, where $R^{31}$ and $R^{32}$ may be the same or different groups and at least one is selected from a $C_2$-$C_{10}$ alkyl group, for instance $R^{31}$=isobutyl and $R^{32}$=methyl.

Preferably, the suitable source of formaldehyde is selected from 1,1 dimethoxymethane, higher formals of formaldehyde and methanol, $CH_3$—O—$(CH_2$—$O)_i$—$CH_3$ where i=2, formalin or a mixture comprising formaldehyde, methanol and methyl propionate.

Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%:0.03 to 20%:35 to 60% by weight. Most preferably, by the term formalin is meant a mixture of formaldehyde:methanol:water in the ratio 35 to 55%:0.05 to 18%: 42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Therefore, according to a still further aspect of the present invention there is provided a process for preparing and purifying an ethylenically unsaturated acid or ester of the following formula:—

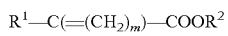

wherein $R^1$ and $R^2$ are defined in the same way as for the ethylenically unsaturated acid or ester above; and m is 1 or 2; the process comprising the steps of— a) contacting an alkanoic acid or ester of the formula $R^1$—$CH_2$—$COOR^3$, wherein $R^3$ and $R^1$ are as already defined above, with a methylene or ethylene source of formula I, and optionally in the presence of an alkanol to produce an impure ethylenically unsaturated acid or ester of the formula:—

$R^1$—C($=$($CH_2$)$_m$)$COOR^2$;

b) purifying the impure product of step a) contact with an acidic ion exchange resin until the ion exchange resin is at least partially deactivated; and c) treating the at least partially deactivated ion exchange resin with an alkanol of formula $R^4OH$, wherein $R^4$ is an alkyl group with 1 to 12, more preferably 1 to 8, most preferably, 1 to 4 carbon atoms, and a carboxylic acid of formula:—

$R^1$—$CH_2$—COOH to thereby reactivate the acidic ion exchange resin and produce as a by-product an ester of formula:—

$R^1$—$CH_2$—$COOR^4$;

d) optionally hydrolysing the ester of step to produce an acid of formula:—

$R^1$—$CH_2$—COOH;

e) recycling the said ester or acid of step c) or acid of step d) as a reactant in step a) with the proviso that when the ester of step c) is recycled, $R^4$ and $R^3$ are the same alkyl group.

Preferably, in the case of an ester product, $R^4$, $R^3$ and $R^2$ are the same alkyl group.

The invention also extends to the use of the above process step c) to reactivate a deactivated resin bed.

Suitable acids of formula. $R^1$—$CH_2$—COOH or alkanols of formula $R^4OH$ include those listed supra in relation to the first aspect of the present invention.

Preferably, the ethylenically unsaturated acid or ester is selected from methacrylic acid, acrylic acid, met methacrylate, ethyl acrylate or butyl acrylate, more preferably, it is an ethylenically unsaturated ester, most preferably, methyl methacrylate. Accordingly, the preferred ester of formula $R^1$—$CH_2$—$COOR^2$ me thy propionate and the preferred alkanol and carboxylic acid are therefore methanol and propionic acid. However, it will be appreciated that in the production of other ethylenically unsaturated acids or esters, the preferred alkanols or acids will be different. For example, in the production of butyl or acrylate the preferred reactivation agents would be butanol and ethanol respectively with ethanoic acid.

By-products of the reaction in a) above may be the acid of formula:—

$R^1$—$CH_2$—COOH or $R^1$—C($=$($CH_2$)$_m$)COOH

These compounds are produced by the hydrolysis of the corresponding alkyl esters. Advantageously, by reacting these acids with an alkanol of formula $R^4OH$ they may be recycled as reactant and product respectively.

Temperatures and pressures for the reactivation treatment of the acidic ion exchange resin of the present invention are preferably, in the range 20-120° C., more typically, 30-80° C., most typically, 40-70° C. Typically, the reactivation takes place with the reactivation liquid acting under gravity on a substantially vertical column. However, pressure flow is also envisaged. Suitable operating pressures for the reactivation may be in the range $1 \times 10^5$-$10^6$ $Nm^{-2}$, more typically, $1.1 \times 10^5$-$5 \times 10^5$ $Nm^{-2}$, most typically, $1.5 \times 10^5$-$4 \times 10^5$ $Nm^{-2}$.

All of the features contained herein may be combined with any of the above aspects and in any combination.

The invention will now be illustrated by the following examples and figures in which:—

FIG. 1 is a plot of total diene output versus methanol output on a resin bed treated according to the invention.

EXAMPLES

Example 1

A sample of 250 ml of Lewatit K2431 sulphonic acid ion exchange resin was washed with methanol and then MMA, this washing caused the volume to contract to 200 ml. A liquid stream of impure MMA containing 100 ppm hydroquinone (HQ) as stabiliser was passed over the resin at 60° C. at a flow rate of ca 500 ml/hr. Major impurities in this liquid stream were about 80 ppm in sum of cis- and trans-2-methyl-2,4-hexadiene. This flow was maintained for 41 days after which the conversion of these dienes to heavy by-products had fallen to 70%. Thereafter, the flow of the impure MMA stream was stopped and 1.2 kg of methanol were passed through the bed of resin at 50 g/hr. The flow of impure MMA was restarted and the conversion of the dienes rose to 100% and was maintained at this level for a further 5 days. Over the following 15 days the conversion again fell to 70%. The flow was stopped and 2.1 kg of methanol was re-circulated through the resin bed at a flow rate of 250 g/hour for 20 hours. Thereafter the flow of impure MMA was restarted and conversion of the dienes reverted to 100% and was maintained at this level for 3 days.

In the same experiment, isobutyraldehyde precursors were included in the impure MMA, in the form 2-methylpropenol and 2,2'-dimethoxy-propane and isobutyraldehyde. The levels of these three components exiting the resin beds in the two days preceding the methanol treatment and after 42 days were about 48% of the inlet levels. In the two days following the treatment with methanol, the exit level fell to 15% of the inlet level. The exit levels of isobutyraldehyde components prior and post the recycle treatment fell from 45% to 15%.

Example 2

After periodic treatment of a 250 ml bed of Lewatit 2431 resin with methanol when it had become substantially deactivated following prolonged exposure to impure MMA, the feed of impure MMA containing 80 ppm of cis- and trans-2-methyl-2,4-hexadiene was restarted. The initial conversion of dienes was low, but this improved with time. The diene concentration in the exit of the bed fell as the methanol concentration fell as shown in FIG. 1 and in table 1:

| Methanol In Exit from Resin Bed/ppm | Level of Dienes in Exit from Resin Bed/ppm |
|---|---|
| 8651 | 69 |
| 8414 | 72 |
| 5521 | 34 |
| 5326 | 42 |
| 4552 | 24 |
| 4210 | 19 |
| 3739 | 17 |
| 3059 | 9 |
| 2591 | 5 |

Therefore as the level of methanol falls the activity for removal of dienes improves.

Example 3

Comparative 1000 ml of water wet Lewatit K2431 resin (691.1 g) was washed twice with 2.5 wt % HQ in methanol followed by two further washes with 2.5 wt % HQ in MMA. It was used to purify 500 g/hour of impure MMA at 55° C. for a total of 80 days by which time the removal of dienes had dropped to 54%. The resin was then discharged in 9 approximately equal weight segments. Tests of the individual segments showed that segments 1 and 2 from the front of the bed were inactive for removal of dienes whereas the sections further back in the bed were responsible for the limited conversion of dienes observed from the overall bed. Segments 1 and 2 were used for further studies to determine the amount of tarry material which could be removed from aliquots of the deactivated resin by treating with a range of solvent compositions.

In each test, 20 g of the test solvent was added to 3 g of the dry resin beads in a 100 ml round bottomed flask. The flask was heated in a water bath to 60° C. for 30 mins with periodic shaking. The results are shown in Table 2.

TABLE 2

| Wt % levels Methyl Propionate/MMA | Wt of residue extracted from 3 g Resin/mg | mg tar/g resin |
|---|---|---|
| 0/100 | 83.8 | 27.9 |
| 0.2/99.8 | 62.6 | 20.9 |
| 1/99 | 91.1 | 30.4 |
| 5/95 | 84.5 | 28.2 |
| 10/90 | 131 | 43.7 |
| 20/80 | 112.4 | 37.5 |
| 100/0 | 206.4 | 68.8 |

MeP is therefore a much better solvent than MMA.

Example 4

10 ml samples of Segment 2 from example 3 were drained of residual liquid MMA. Three solvent compositions were tried:— Methanol, 50:50 Methanol:MeP and MeP with the intent of discovering which extracted the most tar in the same time. In each experiment, 14 ml of solvent was added to 10 mls of decanted resin to obtain 20 ml of total mixture and then the whole mixture carefully transferred to a 25 ml round bottomed flask. The whole mixture was then heated under reflux for a total of 2 hours with 2 ml samples of solution collected after 0, 15, 30, 60 and 120 minutes. Each 2 ml sample was weighed and left to evaporate and then reweighed to obtain the weight of tar per g of solvent. The results are shown in Table 3.

TABLE 3

| Time (mins) | Methyl Propionate Wt % Tar Dissolved | Methanol Wt % Tar Dissolved | 50:50 wt % Methyl Propionate:Methanol Wt % Tar Dissolved |
|---|---|---|---|
| 0 | 0.00 | 0.00 | 0.00 |
| 15 | 2.17 | 13.90 | 8.99 |
| 30 | 2.95 | 12.57 | 9.36 |
| 60 | 4.41 | 12.44 | 9.44 |
| 90 | | | 9.92 |
| 120 | 5.55 | 18.49 | |
| 342 | | | 10.76 |

Methanol extracted the most tar with 50:50 methanol/MeP the next most effective and MeP the least effective.

Example 5

A 20 ml sample of Lewatit 2621 Acidic Ion Exchange resin from a larger bed of 750 ml resin, which had been used for purifying impure MMA for 30 days at a flow of 550 g/hour impure MMA at 55° C., was treated with a 232 g of propionic acid at 2 g/min in a 50 ml glass column over 2 hours at 25° C. The effluent solution was light yellow in colour. The experiment was repeated with methanol as the solvent instead of propionic acid and the effluent solution was mid brown.

The experiment was repeated with a 2:1 mixture by weight of propionic acid and methanol and the resultant effluent washings from the column were dark brown, becoming lighter as the treatment proceeded.

Weighed samples were collected during the propionic acid/methanol treatment in example 5 as the treatment proceeded and allowed to evaporate to obtain the wt % tar in each. The absorbance at 460 nm for each sample was also measured to relate its colour to the amount of tar present.

TABLE 4

| Time (mins) | Cumulative Mass of Treatment Solvent/g | Wt % Tar Dissolved | Absorbance at 460 nm |
|---|---|---|---|
| 0 | 0 | 0 | 0 |
| 30 | 10.06 | 0.511 | 0.5178 |
| 60 | 39.37 | 0.362 | 0.4221 |
| 90 | 82.50 | 0.145 | 0.1027 |
| 120 | 120.04 | 0.067 | 0.0634 |
| 180 | 159.61 | 0.047 | 0.0482 |
| 240 | 253.53 | 0.036 | 0.0323 |
| 300 | 368.74 | 0.011 | 0.0027 |
| 360 | 486.41 | 0.008 | 0.0009 |

The absorbance at 460 nm is directly proportional to the quantity of tar in the sample, showing that colour is a good measure of the quantity of tar in the solution. The three extractions carried out in this example show that propionic acid is much less effective as a solvent than methanol, whereas mixtures of methanol and propionic acid are more effective than methanol.

Example 6

A 750 ml bed of Lewatit K2431 acidic ion exchange resin was used to treat 500 g/h of impure MMA at 55° C. for 30 days. During this time, the resin was treated once, after 18 days for 6 hrs at 2.5 liters methanol/hr at 25° C., followed by approximately 3 bed volumes of pure MMA at 180 ml/hour and at 25° C. until the methanol content of the reactor exit solution fell to below 3000 ppm. The feed of impure MMA was then restarted and continued for 27 days until the level of dienes in the exit stream from the resin bed rose above 20 ppm. At this point the treatment process was continued as detailed below. It was then drained and discharged and transferred to a 2 liter round bottomed flask with a mechanical stirrer. Solvents were added to the flask and the contents of the flask were stirred at 25° C. for between 12 and 72 hrs. Samples were taken of the liquor at intervals and evaporated to determine the tar content. At the end of each treatment, the liquid was carefully filtered from the resin using a large Buchner funnel. The solvent filtrate was weighed as was the wet resin. The resin was then put back into the flask and the fresh solvent for the next treatment added.

TABLE 4

| Treatment No. | Solvent | Quantity/ ml | Treatment duration/h | Wt tar removed/ g | Rate of Tar Removal g/h |
|---|---|---|---|---|---|
| 1 | Methanol | 350 | 16.5 | 10.85 | 0.66 |
| 2 | Methanol | 700 | 23.5 | 11.75 | 0.50 |
| 3 | Methanol | 700 | 69.5 | 3 | 0.04 |
| 4 | Methanol + Methyl Propionate 1:1 | 700 | 25 | 1.2 | 0.05 |
| 5 | Methanol | 700 | 43 | 2.4 | 0.06 |
| 6 | Methanol + Water 1:1 | 700 | 23 | 0 | 0.00 |
| 7 | Methanol + Propionic Acid 1:2 | 700 | 17.5 | 11.9 | 0.68 |
| 8 | Methanol + Propionic Acid 1:2 | 700 | 20 | 4.7 | 0.24 |
| 9 | Methanol + Propionic Acid 1:2 | 700 | 23.5 | 3 | 0.13 |
| 10 | Methanol + Propionic Acid 1:2 | 700 | 23.5 | 1 | 0.04 |

As the resin bed is treated it would be expected that the rate of tar removal would diminish. This is evident for methanol in Treatments 1-3. Methyl propionate:methanol and water:methanol mixtures are relatively ineffective. But methanol:propionic acid 1:2 mixture is very effective at removing tar that methanol has failed to remove.

Example 7

A 750 ml bed of Lewatit K2431 was used for 165 days at 55° C. to purify impure MMA at a flow rate of 500 g/h. During this time it was treated with methanol 3 times. After the last treatment it was operated for 15 days to purify impure MMA. It was then treated with a flow of 10 ml/hour methanol at 50° C. This was continued until virtually no further tar was coming off the bed and the eluting solvent was virtually colourless. This part of the treatment took 290 hours. The treatment solvent was then switched to 66.6 wt % propionic acid: 33.3 wt % methanol and the treatment continued at room temperature. After an initial period where the methanol was replaced in the bed by the propionic acid:methyl propionate mixture the colour of the eluting solvent changed in colour from very pale straw to a very dark brown indicating that some further tar was being eluted off the bed. Table 5 shows the tar extraction profile through the two treatments with time.

TABLE 5

| Time/h | Solvent | Treatment Temp/C. | Cumulative Wt Tar Removed/g | Rate of Removal of Tar/mg/h |
|---|---|---|---|---|
| 20 | Methanol | 50 | 10.1 | 505 |
| 40 | Methanol | 50 | 12.7 | 130 |
| 60 | Methanol | 50 | 15.7 | 150 |
| 80 | Methanol | 50 | 17.1 | 70 |
| 100 | Methanol | 50 | 17.8 | 35 |
| 150 | Methanol | 50 | 19.1 | 26 |
| 200 | Methanol | 50 | 19.9 | 16 |
| 250 | Methanol | 50 | 20.4 | 10 |
| 290 | Methanol | 50 | 20.7 | 8 |
| 300 | 2:1w/w Propionic Acid:Methanol | 20 | 20.8 | 10 |
| 350 | 2:1w/w Propionic Acid:Methanol | 20 | 24.1 | 66 |
| 400 | 2:1w/w Propionic Acid:Methanol | 20 | 27.6 | 70 |
| 450 | 2:1w/w Propionic Acid:Methanol | 20 | 29.2 | 32 |
| 500 | 2:1w/w Propionic Acid:Methanol | 20 | 30.4 | 24 |
| 550 | 2:1w/w Propionic Acid:Methanol | 20 | 30.8 | 8 |
| 580 | 2:1w/w Propionic Acid:Methanol | 20 | 31.95 | 2 |
| 590 | 2:1w/w Propionic Acid:Methanol | 50 | 31.2 | 25 |

The rate of removal of tar accelerates from less than 10 mg per hour at the end of the methanol treatment at 50° C. to 70 mg per hour following introduction of the 2:1 w/w propionic acid:methanol mixture at 20° C. removing an extra 50% of residues which would not have been removed by the methanol alone. During the last few hours, the temperature was raised to 50° C.; a large rate of increase in tar removal rate was observed.

Example 8

A 750 ml bed of Lewatit K2621 was used for 15.5 days at 50° C. to purify impure MMA at a flow rate of 560 g/h. During this time it removed a cumulative total of 12.7 g of trans & Cis 2-methyl-2,4-hexadiene and 8.7 g of isobutyraldehyde before becoming deactivated. The bed was then reactivated by treating with 7×1 liter of methanol at 50° C. The bed was then used for a further 6 cycles of MMA purification each time until the bed was deactivated, whereupon it was reactivated by treating with either methanol or a methanol propionic acid mixture. Table 9 compares the capacity of the bed to remove the dienes and isobutyraldehyde after each reactivation procedure.

TABLE 6

| Cycle | Days Purifying MMA | Reactivation Solvent Prior to Purification | Mass Dienes Removed in cycle/g | Mass Isobutyral Removed in cycle/g |
|---|---|---|---|---|
| 1 | 15.5 | N/A | 12.7 | 8.7 |
| 2 | 10.5 | 7 × 1 l Methanol | 11.3 | 14.1 |
| 3 | 8.5 | 3.6 l Methanol | 12.0 | 10.4 |
| Avg | 11.4 | | 12.0 | 11.1 |
| 4 | 8.6 | PA & Methanol 2:1 w/w | 17.3 | 24.1 |
| 5 | 23.2 | Esterification Mix[1] | 19.3 | 9.9 |
| 6 | 14.5 | Esterification Mix[1] | 16.4 | 16.0 |
| 7 | 15.9 | Esterification Mix[1] | 17.9 | 12.0 |
| Avg | 15.6 | | 17.7 | 15.5 |

[1]Approximately 0.2% water, 25% methanol, 47% propionic acid, 6% methyl methacrylate, 3% methacrylic acid, 8% methyl-2,5-dimethyl-4-pentenoate isomers and 11% other heavy compounds, predominantly methyl esters of complex aliphatic acids.

Following reactivation of the resin bed by treating with propionic acid(PA) and methanol mixtures, the resin bed was able to remove on average 40 to 45% more dienes and isobutyral than treating with methanol alone. It was found in cycles 5 to 7, that esterification of a by-product stream rich in propionic acid with methanol could still be achieved using the deactivated resin bed. It was, therefore, found to be advantageous to use the deactivated resin bed to recover the propionic acid in this stream as methyl propionate which could be recycled as a reactant in the production of methyl methacrylate. A further advantage in the reactivation of the resin bed using this stream was the avoidance of unnecessary treatment streams and the removal from the process of the tarry residues as part of an existing heavy by-product stream.

Example 9

An esterification mixture of approximate composition 0.2% water, 25% methanol, 47% propionic acid, 6% methyl methacrylate, 3% methacrylic acid, 8% methyl-2,5-dimethyl-4-pentenoate isomers and 11% other heavy compounds, predominantly methyl esters of complex aliphatic acids, was fed at a rate of 100 g/hour at 50° C. to a 750 ml bed of Lewatit 2431 sulphonic acid ion exchange resin which had previously been used to purify impure MMA at a flow of 500 g/hour and 55° C. and whose activity had decayed until over 20 ppm dienes remained in the exit stream from the ion exchange resin. The exit stream from the initially deactivated ion exchange resin had an approximate composition: 9% water, 10% methanol, 45% methyl propionate, 11% propionic acid, 8% methyl methacrylate, 2% methacrylic acid, 5% methyl 2,5-dimethyl-4-pentenoate isomers and 10% other heavy compounds. Thus, the spent bed has converted over 75% of the propionic acid to methyl propionate and water.

The weight of tars produced from the exit stream of this resin bed was analysed by allowing evaporation to dryness followed by weighing the involatile components. The time dependence of extraction of the tars is shown in table 7.

TABLE 7

| Time/h | Solvent | Treatment Temp./C. | Cumulative Wt Tar Removed/g | Rate of Removal of Tar/mg/h |
| --- | --- | --- | --- | --- |
| 20 | Esterification Mixture | 50 | 9.6 | 480 |
| 40 | Esterification Mixture | 50 | 15.8 | 310 |
| 60 | Esterification Mixture | 50 | 19.6 | 190 |
| 80 | Esterification Mixture | 50 | 21.1 | 75 |
| 100 | Esterification Mixture | 50 | 22.1 | 50 |
| 150 | Esterification Mixture | 50 | 23.7 | 32 |
| 200 | Esterification Mixture | 50 | 24.4 | 14 |
| 250 | Esterification Mixture | 50 | 24.9 | 10 |
| 290 | Esterification Mixture | 50 | 25 | 3 |

The total quantity of tar removed and the rate of tar removal are superior to the rate of removal of tars from an equivalent sample of resin as shown in table 5. An additional advantage of operating the process using the treatment mixture of example 9 over that in example 7 is that the product in the effluent, produced by reaction on the resin bed can be recycled.

Following the period of 290 hours during which the resin bed was cleaned and also used to esterify a crude propionic acid stream it was subsequently treated with pure MMA until the level of methanol in the MMA stream exit from the bed contained below 3000 ppm methanol. It was then again used to purify an impure MMA stream at a flow rate of 500 g/h at 55° C. The lifetime of the bed before the levels of dienes rose to over 20 ppm was found to be 35% longer using the methanol-propionic acid containing stream than when it had been reactivated with pure methanol.

Example 10

Two Lewatit acidic ion exchange resins were used for purification of impure methyl methacrylate containing diene impurities until the level of dienes in the exit stream from the resin bed rose to above 20 ppm. They were then treated firstly with methanol until the methanolic solution was practically colourless. Following this, they were treated with pure MMA until the methanol level fell to below 3000 ppm in the MMA stream. The times taken to achieve this are shown in the table below:

TABLE 8

| Resin | Time to <3000 ppm Methanol/hours |
| --- | --- |
| K2431 | 103 |
| K2621 | 48 |

The physical properties of the two resins are compared in table 9

TABLE 9

| | K2431 | K2621 |
| --- | --- | --- |
| Density g/cm3 | 1.15 | 1.15 |
| Surface Area m2/g | 25 | 33 |
| Pore Volume/cm3/g | 0.35 | 0.45 |
| Pore Diameter/nm | 40 | 41 |
| % Water/g of wet resin | 60-65 | 57-63 |

The most significant difference between the two resins is the pore volume which is nearly 30% higher for the K2621 compared to K2431. This observation explains the much more rapid elution of methanol from the K2621 acidic ion exchange resin.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for the reactivation of an acidic ion exchange resin that has been at least partially deactivated by contact with an impure ethylenically unsaturated acid comprising organic target impurities or impure ethylenically unsaturated ester comprising organic target impurities comprising the step of:
   contacting the at least partially deactivated resin with a $C_1$-$C_{12}$ aliphatic alkanol to thereby increase the activity thereof.

2. A process for the reactivation of an acidic ion exchange resin according to claim 1, wherein the acidic ion exchange resin is in the form of a packed resin bed.

3. A process for the reactivation of an acidic ion exchange resin according to claim 2, wherein the resin bed is at least 10% reactivated by the process of the invention.

4. A process for the reactivation of an acidic ion exchange resin according to claim 1, wherein the volume of alkanol is such as will cause the deactivated bed to be sufficiently reactivated and to sufficiently remove the accumulated impurities.

5. A process for the reactivation of an acidic ion exchange resin according to claim 1, wherein at least one carboxylic acid is also present with the alkanol in the reactivation process.

6. A process for the reactivation of an acidic ion exchange resin according to claim 5, wherein the volume of alkanol or alkanol and carboxylic acid is such as will cause the deactivated bed to be sufficiently reactivated and to sufficiently remove the accumulated impurities.

7. A process for the reactivation of an acidic ion exchange resin according to claim 1, wherein the impure ethylenically unsaturated product of the present invention is produced by condensation of formaldehyde with methyl propionate to produce methyl methacrylate (MMA).

8. A process for the reactivation of an acidic ion exchange resin according to claim 5, wherein the alkanol or alkanol and carboxylic acid is introduced to the resin in the form of a reactivation liquid.

9. A process for the reactivation of an acidic ion exchange resin according to claim 8, wherein the molar concentration of the alkanol in the reactivation liquid is at least 10 mol %.

10. A process for the reactivation of an acidic ion exchange resin according to claim 8, wherein the molar concentration of the carboxylic acid in the reactivation liquid is at least 2.5 mol %.

11. A process for the reactivation of an acidic ion exchange resin according to claim 1, wherein the impure ethylenically unsaturated acid or ester is produced via the reaction of a suitable source of formaldehyde in the presence of a catalyst with a carboxylic ester.

12. A process for the reactivation of an acidic ion exchange resin according to claim 1, wherein the resins have been used to treat one or more target impurities in the impure ethylenically unsaturated liquid which treatment has led to deactivation of the resin.

13. A process for the reactivation of an acidic ion exchange resin according to claim 12, wherein suitable target impurities are selected from the list consisting of:
   optionally substituted $C_4$-$C_{20}$ dienes; optionally substituted $C_6$-$C_{20}$ trienes; optionally substituted unsaturated aldehydes and ketones; divinyl ketone, ethyl vinyl ketone, ethyl isopropenyl ketone, 3-methylene 1-hexen-4-one, methacrolein and isobutanol; pentenals; and a source of isobutyraldehyde.

14. A process for the reactivation of an acidic ion exchange resin according to claim 1, wherein the ion exchange resin is a sulphonic acid ion exchange resin.

15. A re-activated resin produced by a process according to claim 1.

* * * * *